United States Patent
Tournilhac

(10) Patent No.: US 7,153,517 B2
(45) Date of Patent: Dec. 26, 2006

(54) COSMETIC COMPOSITION STRUCTURED BY A THERMOTROPIC LIQUID CRYSTAL POLYMER

(75) Inventor: Florence Tournilhac, Paris (FR)

(73) Assignee: L'Oreal, Paris (FR)

( * ) Notice: Subject to any disclaimer, the term of this patent is extended or adjusted under 35 U.S.C. 154(b) by 327 days.

(21) Appl. No.: 10/169,093

(22) PCT Filed: Nov. 9, 2001

(86) PCT No.: PCT/FR01/03495

§ 371 (c)(1),
(2), (4) Date: Jul. 10, 2002

(87) PCT Pub. No.: WO02/38112

PCT Pub. Date: May 16, 2002

(65) Prior Publication Data

US 2003/0017182 A1  Jan. 23, 2003

(30) Foreign Application Priority Data

Nov. 10, 2000 (FR) ................................ 00 14503

(51) Int. Cl.
*A61K 6/00* (2006.01)
(52) U.S. Cl. ...................................... 424/401; 424/400

(58) Field of Classification Search ................ 424/401, 424/70.1, 64, 78.08, 70.12
See application file for complete search history.

(56) References Cited

U.S. PATENT DOCUMENTS 5,599,555 A * 2/1997 El-Nokaly ................... 424/488

FOREIGN PATENT DOCUMENTS

| EP | 0 529 597 | 3/1993 |
|----|-----------|--------|
| EP | 0 815 826 | 1/1998 |
| EP | 0 923 928 | 6/1999 |
| EP | 0 950 392 | 10/1999 |
| EP | 0 953 330 | 11/1999 |
| FR | 2 772 600 | 6/1999 |
| WO | 95 11000 | 4/1995 |

* cited by examiner

*Primary Examiner*—Thurman K. Page
*Assistant Examiner*—Eric E. Silverman
(74) *Attorney, Agent, or Firm*—Oblon, Spivak, McClelland, Maier & Neustadt, P.C.

(57) ABSTRACT

The present invention relates to a care and/or make-up composition for the skin and/or lips of human beings, containing a liquid fatty phase comprising at least one anhydrous solvent, structured by a thermotropic liquid crystal polymer in order to obtain media having approximately the consistency of a gel at ambient temperature and that of a fluid when applied to the skin or lips of human beings.

25 Claims, No Drawings

COSMETIC COMPOSITION STRUCTURED BY A THERMOTROPIC LIQUID CRYSTAL POLYMER

The present invention relates to a care composition and/or skin and/or lip make-up composition for human beings containing a liquid fatty phase comprising at least one anhydrous solvent, structured by a thermotropic liquid crystal polymer in order to obtain media having approximately the consistency of a gel at ambient temperature and that of a fluid when applied to the skin or lips of human beings.

By liquid fatty phase, in the sense of the application, is meant a liquid fatty phase at ambient temperature (about 25° C.), composed of one or more liquid fatty bodies at ambient temperature, also called oils, which are mutually compatible.

By structured fatty phase, is meant in the sense of the application, a fatty phase which has the consistency of a gel at ambient temperature.

The liquid crystal polymers, also called LCP for Liquid Crystal Polymers are polymers exhibiting incipient organization in the melted state which results in mesophases or mesomorphic phases or even "liquid crystal" phases. The liquid crystal polymers are grafted with rigid molecules having a marked anisotropic, elongated or flat form, like that of a rod or a disk, the cause of the appearance of the mesomorphic phases.

By thermotropic liquid crystal polymer (LCP) is meant a liquid crystal polymer for which the transition between the solid state and the liquid state is made by heating before thermal degradation. The mesomorphic phases are present in a range of temperatures having for lower limit the vitreous transition temperature $T_g$ of the thermotropic liquid crystal polymers and for upper limit their clarification temperature $T_{cl}$.

The clarification temperature is the temperature above which the total rupture of the orientation order is produced, the rupture of the short distance position order occurring at temperatures equal to or lower than the clarification temperature $T_{cl}$. The rupture of the orientation order results in the disappearance of the mesophases: the polymer becomes liquid and isotropic. The clarification temperature $T_{cl}$ is also called isotropization temperature.

By medium having approximately the consistency of a gel is meant in the sense of the application a medium structured by a thermotropic liquid crystal polymer exhibiting an at least two dimensional mesomorphic phase.

The smectics are at least two dimensional mesomorphic phases having layered structures. They possess an order of orientation and a short distance order of position over at least one dimension. The molecules which compose these phases are represented in the form of rods, the centres of gravity of which are situated in equidistant and parallel planes, thus forming superposed layers. The molecules possess a preferred axis of orientation with respect to these layers.

By medium having approximately the consistency of a fluid is meant in the sense of the application a medium structured by a thermotropic liquid crystal polymer exhibiting an at most one dimensional mesomorphic phase.

The nematics are one dimensional mesomorphic phases. They possess is only one order of orientation. The molecules which compose these phases exist in the form of rods randomly distributed and oriented according to a privileged axis, also called directing axis.

Certain cosmetic solvents are difficult to structure, especially to gelify and/or rigidify, in particular the anhydrous solvents such as the hydrocarbon and siliconized oils.

In general, in the cosmetic or dermatological products, solid ingredients are used for the structuring of the liquid fatty phase, in particular mineral (silica) or organic (waxes) particles, which are concentrated until the desired texture is obtained. The application to the skin of such products leads to deposits which spread with difficulty and which do not form a continuous film. In addition, these products constitute care and/or make-up products which transfer.

The object of the invention is therefore a cosmetic composition which remedies these disadvantages.

In particular, the object of the invention is a cosmetic composition comprising a liquid fatty phase containing at least one anhydrous solvent, structured by a thermotropic liquid crystal polymer, comprising a main macromolecular chain and thermotropic mesogenic groups grafted as side chains on to the macromolecular chain.

These liquid crystal polymers ensure a physical cross-linking of the cosmetic composition, the degree of which varies as a function of the temperature. They lead to a modulation of the rheological properties of the film deposited as a function of the temperature, in particular on the skin and/or lips of humans.

A further object of the invention is the use of a cosmetic composition according to the invention for the manufacture of care and/or make-up products.

The thermotropic liquid crystal polymers comprising thermotropic mesogenic groups grafted as side chains on to the main macromolecular chain are thermotropic LCPs with side chains, also called SCLCP or "Side Chain LCP".

The use of the SCLCPs in the cosmetic applications is also known from the prior art. Thus, the SCLCPs are used for their antimicrobial action in the Japanese patent JP-5017396, or for their action facilitating dental hygiene in the international patent application WO-97/45095. The optical properties of the insoluble LCPs are related in the international patent applications WO-95/08786 and WO-94/22976, as well as in the British patent GB-2282146.

However, nothing is said in all of these documents concerning the rheological properties of the SLCPs used in these applications.

Moreover, the documents of the prior art mentioning more specifically the mechanical properties of the LCPs only relate to main chain LCP polymers having a high vitreous transition temperature such as the polyaramides of the Kevlar type and principally involved in materials or matrices in order to reinforce their mechanical properties, which is not the object of the invention.

The aims of the present invention are attained by producing a cosmetic composition containing at least one liquid fatty phase comprising at least one anhydrous solvent selected from the hydrocarbon and siliconized oils, structured by at least one liquid crystal polymer, thermotropic and soluble in the anhydrous solvent and comprising:

a main macromolecular chain thermotropic mesogenic groups grafted on to the macromolecular chain, with a degree of grafting of at least 10%, and preferably at least 15%, said polymer having a vitreous transition temperature $T_g$ equal to or less than 15° C. and a clarification temperature $T_{cl}$ higher than 45°C., and exhibiting a phase transition between an ordered mesomorphic phase $S_2$ with at least two dimensions and a poorly ordered mesomorphic phase $S_1$ with one dimension, with a transition temperature $T_{S2/S1}$ higher than 25° C. and equal to or less than 40° C., and preferably between 30 and 36° C.

Generally, the ordered mesomorphic phase $S_2$ with at least two dimensions is a smectic phase, and the poorly ordered mesomorphic phase $S_1$ with one dimension is a nematic phase N.

As examples, mention may be made of two-dimensional smectics, the smectics A and C, designated $S_A$ and $S_{cl}$ respectively. The smectics A and C possess an order of orientation and short distance order of position. The molecules which compose them form superposed parallel layers in which they are randomly distributed, while being oriented on average perpendicularly to the layers in the smectics A and inclined with respect to the perpendicular of the layers in the smectics C.

As examples, mention should be made of tri-dimensional smectics, the smectics B, designated $S_B$. The smectics B possess an order of orientation and a double short distance order of position, because the molecules are not distributed randomly in the layers, but form a hexagonal mesh.

The main macromolecular chain is a flexible polymer which constitutes the skeleton of the liquid crystal polymer according to the invention. The presence of this skeleton is an order factor. In an enhanced manner, it orients the mesogenic groups, which of themselves tend to order themselves to form mesophases.

Of the macromolecular chains, mention may be made of the acrylic polymers such as the polyacrylates, the polymethacrylates and the polychloroacrylates, the polysiloxanes and the cyclosiloxanes, the polystyrenes, the polyvinylethers, the polyoxiranes, the polyalkenes, the polynitrile, the polyacrylamides, the polyphosphazenes, the polyurethanes, the polymalonates and the poly(vinylether-alt-maleic anhydride).

Preferably, the macromolecular chain is a polydimethylsiloxane, in particular a polydimethylsiloxane.

Particularly preferably, the macromolecular chain is a polydimethylsiloxane comprising more than 50 motifs.

The mesogenic groups are rigid groups having a marked anisotropic form, the cause of the appearance of the mesomorphic phases in the domain of the temperature ranging from the vitreous transition temperature $T_g$ to the clarification temperature $T_{cl}$ of the liquid crystal polymer according to the invention.

The mesomorphic phases exist and are stable for a broad range of grafting of the mesogenic groups on to the skeleton.

By range of grafting is meant in the context of the application the percentage of monomeric motifs of amesogenic group grafted on to the macromolecular chain.

For example, a degree of grafting of 25% means that a mesogenic group is grafted on to one monomer motif out of four, and a degree of grafting of 60% means that mesogenic groups are grafted on to three monomeric motifs out of five.

Generally speaking, a minimal degree of grafting of 10% and preferably of 15% is needed. When the degree of grafts is lower than 10%, there is practically little or no formation of mesophases at all.

Advantageously, the degree of grafting of the thermotropic mesogenic groups on to the macromolecular chain varies from 10% to 70%, preferably from 15% to 65%, and better still from 25 to 60%.

The preferred mesogenic groups also called grafts are defined by the following structure:

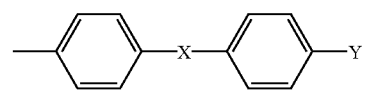

where X designates a covalent bond or a group

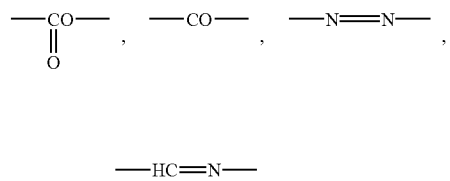

Y is a terminal polar or apolar group such as an alkyl (methyl, ethyl, propyl), alkoxy (methoxy, ethoxy, propoxy), —CN or —NO$_2$ group.

The rigidity of the mesogenic group is ensured by the aromatic rings connected by the element X.

The element Y is a terminal group which promotes the smectic phases if it is polar and the nematic phases if it is weakly or not at all polar. The polarity of the element Y also has an incidence on the thickness of the smectic layers.

The mesogenic groups are linked to the macromolecular chain through the intermediary of a spacer.

The spacer is a short flexible sequence, preferably selected from methylene, oxymethylene, oxyethylene and dimethylsiloxane oligomers.

The spacer has a minimal length which generally corresponds to three monomer motifs.

The preferred spacers are:

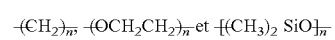

Where n is an integer from 3 to 11.

Advantageously, the liquid crystal polymer comprises maximally 50% of mesogenic groups with respect to the total mass of the polymer, and preferably maximally 30%.

A particularly appreciated liquid crystal polymer is defined by the following structure:

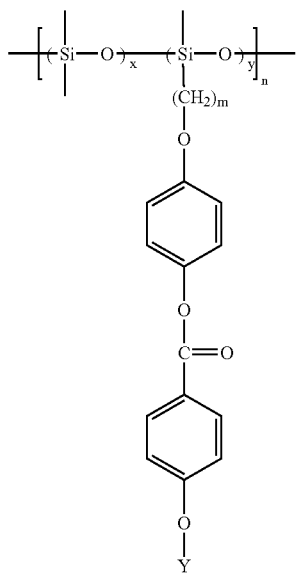

where Y is a radical such as defined above, m is an integer greater than 3 n is an integer greater than 50 x and y are such that the liquid crystal polymer comprises maximally 50% of mesogenic groups with respect to the total mass of the polymer, and preferably maximally 30%.

This polymer is obtained for example by the following synthesis, consisting successively of the steps of:

cationic polymerization of polydimethylsiloxane, hydrogenation of polydimethylsiloxane, then grafting of the thermotropic mesogenic groups, linked covalently to the spacers, to polydimethylsiloxane by hydroxylation.

The fatty phase contains at least one anhydrous solvent selected from the hydrocarbon and siliconized oils, usable in cosmetics. These oils may be polar or non-polar, volatile or non-volatile.

Of the polar oils, mention may be made of the hydrocarbon oils bearing ester, ether, acid, alcohol functions or their mixtures, such as for example:

the hydrocarbon vegetable oils with high triglyceride content constituted of fatty acid esters and glycerol the fatty acids of which may have chains of varying lengths, these latter being linear or branched, saturated or unsaturated; these oils are in particular the oils of wheat germ, maize, sunflower, karite, castor, sweet almonds, macadamia, apricot, soya, colza, cotton, lucerne, poppy, pumpkin, sesame, squash, avocado, hazelnut, grape seed or black currant seed, evening primrose, millet, barley, quinoa, olive, rye, saffron, candlenut, passion flower, rose muscat; or also the triglycerides of caprylic/capric acids like those sold by the Stearineries Dubois company or those sold under the designations Miglyol™ 810, 812 and 818 by the Dynamit Nobel company;

synthetic oils of the formula $R_1COOR_2$ in which $R_1$ represents a higher fatty acid residue, linear or branched, consisting of from 7 to 19 carbon atoms, and $R_2$ represents a branched hydrocarbon chain containing from 3 to 20 carbon atoms, like for example Purcellin oil (octanoate of ketostearyl), isononyl isononanoate and the alkyl benzoates;

synthetic esters and ethers like isopropyl myristate, ethyl-2-hexylpalmitate, octanoate, decanoates or ricinoleates of alcohols or polyalcohols, hydroxylated esters like isostearyl lactate, di-isostearyl malate; and the esters of pentaerythritol;

$C_8$ to $C_{26}$ fatty alcohols such as oleic alcohol; and their mixtures.

Of the apolar oils, mention may be made of the volatile or non-volatile, linear or cyclic, silicone oils, liquid at ambient temperature such as:

the polydimethylsiloxanes (PDMS), comprising alkyl, alkoxy or phenyl groups, side chain and/or silicon chain terminating and having from 2 to 24 carbon atoms;

the phenylated silicones like the phenyl trimethicones, the phenyl dimethicones, the phenyl trimethylsiloxy diphenylsiloxanes, the diphenyl dimethicones, the diphenyl methyldiphenyl trisiloxanes, the 2-phenylethyl trimethylsiloxysilicates;

the hydrocarbons or the fluorinated hydrocarbons, linear or branched of synthetic or mineral origin, such as the paraffin oils (for example the isoparaffins), and the volatile or non-volatile aliphatic hydrocarbons (for example, isododecane) and their derivatives, vaseline, the polydecenes, hydrogenated polyisobutene such as Parleam™, squalane, and their mixtures.

The preferred silicone oils, and in particular those structured by the liquid crystal polymers according to the invention are selected from the polydimethylsiloxanes (PDMS), bearing alkyl, alkoxy or phenyl groups, side chain and/or siliconized chain terminating and having 2 to 24 carbon atoms and the phenylated silicones like the phenyl trimethicones, the phenyl dimethicones, the phenyl trimethylsiloxy diphenylsiloxanes, the diphenyl dimethicones, the diphenyl methyldiphenyl trisiloxanes, the 2-phenylethyl trimethylsiloxysilicates.

The anhydrous solvent may be a mixture containing a hydrocarbon oil selected from the aromatic esters and preferably an alkyl benzoate.

The apolar media structured by the liquid crystal polymers according to the invention may be constituted of completely apolar mixtures of silicone and hydrocarbon oils with aromatic esters such as an alkyl benzoate.

The composition of the invention may include, in addition, any additive usually used in the field concerned, selected in particular from water optionally thickened or gelified by an aqueous phase thickening agent or a gelifying agent, the antioxidants, the essential oils, the preservatives, the perfumes, the neutralizers, the liposoluble polymers, the cosmetic or dermatological active agents like for example the emollients, the hydrating agents, the vitamins, the essential fatty acids, the solar filters and their mixtures.

Advantageously, the composition also contains at least one cosmetic or dermatological active agent.

Naturally, the man skilled in the art will take care to select the possible supplementary additives and their quantities so that the advantageous properties of the composition according to the invention are not or not substantially impaired by the addition envisaged.

When the composition according to the invention is anhydrous, it is available in the form of a gel at ambient temperature and in that of a fluid at the temperature of the skin and/or lips of humans.

Otherwise, the composition according to the invention is available in the form of a water-in-oil emulsion (W/O) or an oil-in-water (OQN) emulsion, the consistency of which is approximately that of a gel at ambient temperature and that of a fluid at the temperature of the skin and/or lips of human beings.

The application of this composition to the skin and/or the lips, which have a temperature ranging from about 30 to 36° C. necessarily leads to a phase transition of the liquid crystal polymer according to the invention, in particular a smectic-nematic transition. This phase transition makes it possible to pass from a consistency corresponding approximately to that of a gel at ambient temperature to a more fluid consistency on the skin, thus facilitating the spreading of the composition. The application of this composition leads to deposits forming a continuous and homogeneous film on the skin and/or lips and which does not transfer.

The composition according to the invention may also contain a colouring material. This latter can be selected from the lipophilic colouring materials, the hydrophilic colouring materials, the pigments and the pearlescent preparations usually used in cosmetic or dermatological compositions, and their mixtures. This colouring material is usually present to the extent of 0 to 30% of the total weight of the composition.

The liposoluble colouring materials are, for example, Sudan red, DC Red 17, DC Green 6, β-carotene, soya oil, Sudan brown, DC Yellow 11, DC Violet 2, DC orange 5, quinoline yellow.

The pigments may be white or coloured, mineral and/or organic, coated or not. Of the mineral pigments, mention may be made of titanium dioxide, optionally surface-treated, the oxides of zirconium or cerium, as well as the oxides of iron or chromium, manganese violet, ultramarine blue, chromium hydrate and ferric blue. Of the organic pigments, mention may be made of carbon black, the pigments of the organic lake type of barium, strontium, calcium or aluminium including those subjected to FDA certification as well as those exempt from certification such as cochineal red-based lacs.

The pearlescent pigments can be selected from the white pearlescent pigments such as mica coated with titanium or bismuth oxychloride, the coloured pearlescent pigments such as titanium mica with iron oxides, titanium mica with in particular ferric blue or chromium oxide, titanium mica with an organic pigment of the type previously mentioned as well as the bismuth oxychloride based-pearlescent pigments.

The composition according to the invention may be presented in the form of a dermatological composition or care composition for the keratinic matter like the skin (care creams for the skin), and/or the lips (balm for the lips, protecting the lips from the cold and/or the sun and/or the wind).

The composition of the invention may also be available in the form of a coloured make-up product optionally possessing care or treatment properties, which can be applied to the skin (foundation make-up) and the lips (lipstick).

Naturally, the composition of the invention must be cosmetically or dermatologically acceptable, namely must contain a non-toxic physiologically acceptable medium and be capable of being applied to the skin and/or the lips of human beings.

The composition of the invention can be manufactured by the following process:
 dissolution consisting of heating of the composition to a temperature higher than the clarification temperature of the thermotropic liquid crystal polymer, and
 cooling of the composition to ambient temperature.

The object of the invention is also a cosmetic method for the care and/or treatment and/or make-up of the keratinic matter of human beings and in particular of the skin and lips, comprising the application to the keratinic matter of the composition, in particular the cosmetic composition, such as defined above.

The compositions according to the invention are particularly suitable for the manufacture of care and/or make-up products, in particular in lipsticks, foundation make-up and mascaras.

The following examples illustrate the invention without however limiting its scope. In these examples, unless indicated otherwise, the proportions of the constituents are expressed in weights.

EXAMPLE 1

Preparation of a Grafted PDMS Having a Degree of Grafting of 60%

1. Constitutive Elements of the Elastomers

The preparation of the LCPs requires the prior synthesis of the polymer skeletons and the mesomorphic groups.

1.1. Synthesis of the copoly(methylhydrogenodimethyl) siloxane prepolymers

Their synthesis (scheme 1) is performed by means of an acid-catalysed reaction between a cyclic tetramer, octamethylcyclotetrasiloxane (Petrach), designated D4, and commercial linear polymethylhydrogenosiloxanes (Petrach) 35 and 67 motifs long (depending on the desired chain length) designated PMHS35 and PMHS67, respectively.

Scheme I -
Production of linear copolysiloxanes

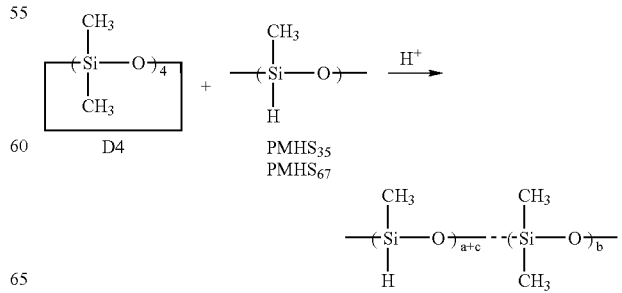

The cationic polymerization of the polysiloxanes has been widely studied and the mechanism shown in scheme 11 has been proposed.

Scheme II -
Mechanism of cationic polymerization of the polysiloxanes

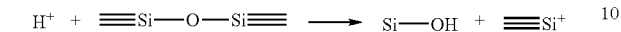

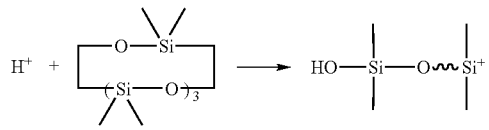

Propagation

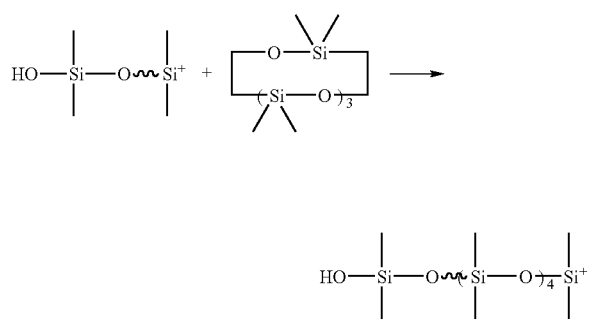

Rétrocission ("backfitting")

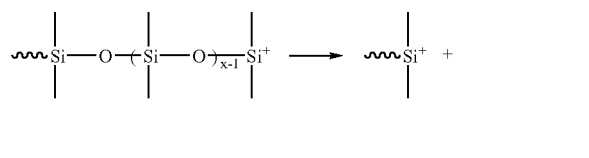

Transfert

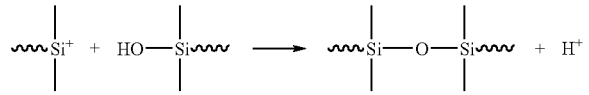

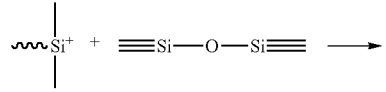

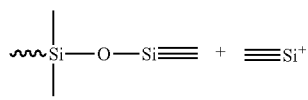

-continued

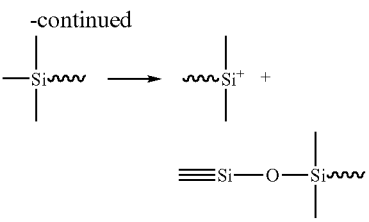

It has been shown that the cyclic oligomers (D4) were first inserted in one piece and that the motifs were then redistributed during a backfitting step. This step is crucial because in the case where it is incomplete, the reactive silane units would not be statistically distributed along the length of the chain. A LCP synthesized with chains thus formed would be inhomogeneous, constituted of regions rich in mesogenic units and regions constituted of dimethylsiloxane units.

The procedure used leads to the synthesis of statistical copolymers, the degree of polymerization of which is maximally 110.

Procedure

Introduce the catalyst (Spherosyl™ acid resin supplied by Rhône Poulenc) into a 25 ml Erlenmeyer flask equipped with a septum and vacuum tap and containing a magnetic stirrer. Purge three times with U nitrogen. The proportion of catalyst is 2 g per 100 g of mixture. Heat to 60° C. in an oil bath then add the reagents D4 to PMHS in the desired proportion through the septum. Stir for three days at 60° C.; allow to cool. Reduce the viscosity of the medium by adding several cm$^3$ of toluene. Filter the mixture through a frit coated with resin (Decalite™ Speed Plus). Eliminate the oligomers and cyclic compounds formed at the rotary evaporator (60° C. for half a day). The product obtained is filtered through a microfilter (Millipore™ porosity 0.2 μm). The yield of this reaction is of the order of 85%.

1.2 Synthesis of the Mesogenic Group

The synthesis of 4-(3-butenyloxy)-phenyl 4-methoxybenzoate or M41 (see scheme III), developed in the laboratory, is carried out in two steps:

1) Synthesis of 4-(3-butenyloxy)phenol (1)

In a three-necked flask equipped with a dropping funnel, a mixture composed of potassium hydroxide (27 mmol) and hydroquinone (45 mmol) is dissolved in 400 ml of absolute ethanol by heating. Add 4-bromo-1-butene (Aldrich) (18 mmol) dropwise. Maintain at reflux for 4 hours. After being cooled and filtered the solvent is evaporated. The mixture is taken up in a solution of ice-cold water. That dissolves a part of the hydroquinone and leads to the appearance of a precipitate containing the desired product. Extract the product with ether. After three washings with water, the organic phase is dried over sodium sulfate then the solvent is evaporated. The phenyl is purified by chromatography on silica gel (eluent: heptane-ether 5/5). The yield of the reaction is of the order of 50%.

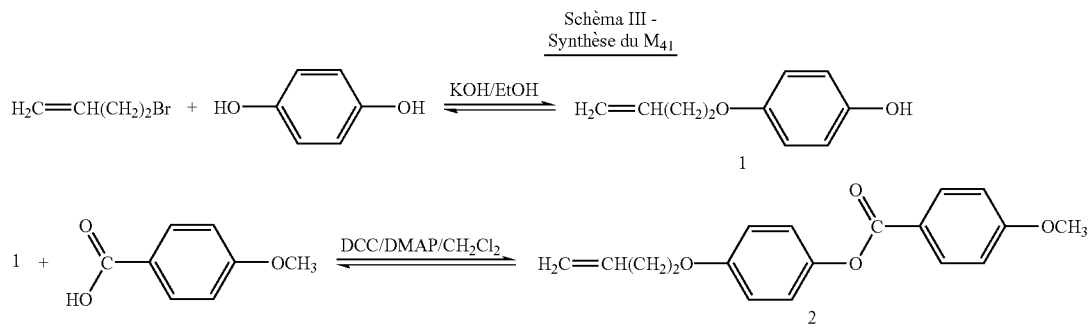

Schéma III -
Synthèse du M41

2) Synthesis of 4-(3-butenyloxy)-phenyl 4-methoxybenzoate (2)

In an Erlenmeyer flask equipped with a magnetic stirrer, add to 60 ml alcohol-free dichloromethane a mixture composed of 30 mmol of phenol, 33 mmol of anisoic acid (Aldrich), 33 mmol of dehydrating agent (N,N'-dicyclohexylcarbodiimide (D.C.C.)) and 3.3 mmol of catalyst (4-dimethylaminopyridine (D.M.A.P.)). The reaction is carried out for 12 hours at ambient temperature and protected from light. The product is filtered in order to eliminate the hydrated D.C.C. After evaporation of the solvent, the pure product is obtained after three recrystallizations from ethanol.

2. Preparation of the LCPs

The mesogenic groups are attached to the copolysiloxane chains by reaction between the vinyl functions and the silane functions, a one-step reaction in a concentrated toluene solution called hydrosilylation.

Procedure

The example presented in this procedure corresponds to that of the synthesis of a LCP containing 60% of actually grafted mesogenic groups, given the reaction yield.

In a 50 ml flat-bottomed reactor equipped with a condenser heated to 60° C. and purged three times with nitrogen, introduce:

250 μm of chains composed of 42% methylhydrogenosiloxane motifs of a mean degree of polymerization of 70 (i.e. 1.43 mmol of Si-H functions), 373 mg of the mesogenic group M41 (i.e. 1.25 mmol), toluene. The homogenization of the mixture is obtained by simple manual stirring of the reactor. The reaction is initiated by dicyclopentadiene platinum II dichloride (D.C.P.) previously dissolved in dry toluene (1 mg/cm³). This catalyst was selected because it can be easily dissolved and leads to quantitative reactions. The stirring is then stopped. The reaction mixture is maintained at 60° C. for one day. The material is obtained then placed in an excess of toluene which should be replaced by fresh toluene every day for one week. This process ensures the removal of molecules which are not attached to the LCP. The sample is then placed in successive baths of a mixture constituted of a poor solvent (methanol) and a good solvent (toluene); the proportion of poor solvent is progressively increased until the material is completely deflated. The sample is finally dried in a vacuum oven at 60° C. for one day.

EXAMPLE 2

Production of a Gel Based on LCP of Example 1

The LCP is introduced with the PDMS of 5 centistokes viscosity in the mass proportions of 90/10 in a tight packaging maintained at 45°C. for 24 h.

EXAMPLE 3

A lipstick composition according to the invention is produced by mixing the following ingredients:
10% polyethylenated wax
32% gel according to Example 2
48% of a mixture of 50% Parleam™ and 50% isododecane
10% pigments.

EXAMPLE 4

A foundation make-up composition according to the invention is produced by mixing the following ingredients:
25% gel according to Example 2
5% of sorbitan monostearate
10% pigments
60% water

The invention claimed is:

1. Cosmetic composition comprising at least one liquid fatty phase comprising at least one anhydrous solvent selected from the group consisting of hydrocarbon oils, siliconized oils and mixtures thereof, structured by at least one liquid crystal polymer, wherein the liquid crystal polymer is thermotropic and soluble in the anhydrous solvent and comprises:
a main macromolecular chain,
thermotropic mesogenic groups grafted onto the macromolecular chain, with a degree of grafting of at least 10%, said polymer having a vitreous transition temperature $T_g$ lower than 15° C. and a clarification temperature $T_{cl}$ higher than 45° C., and exhibiting a phase transition between an ordered mesomorphic phase (S2) with at least two dimensions and a poorly ordered mesomorphic phase (S1) with one dimension with a transition temperature $T_{S2/S1}$ higher than 25° C. and equal to or lower than 40° C.

2. Composition according to claim 1, wherein the ordered mesomorphic phase ($S_2$) with at least two dimensions is a smectic phase S and the poorly ordered mesomorphic phase ($S_1$) with one dimension is a nematic phase N.

3. Composition according to claim 1 wherein the macromolecular chain is a polymer selected from the group consisting of the polyacrylates, the polymethacrylates the polychloroacrylates, the polysiloxanes the polycyclosiloxanes, the polystyrenes, the polyvinylethers, the polyoxiranes, the polyalkenes, the polynitriles, the polyacrylamides, the polyphosphazenes, the polyurethanes, the polymalonates and the poly(vinylether-alt-maleic anhydride).

4. Composition according to claim 3, wherein the macromolecular chain is a polydialkylsiloxane.

5. Composition according to claim 1, wherein the degree of grafting of the thermotropic mesogenic groups on to the macromolecular chain varies from 10% to 70%.

6. Composition according to claim 1, wherein the thermotropic mesogenic groups are defined by the following structure:

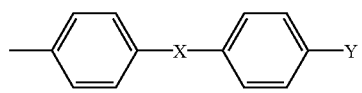

X designates a covalent bond or a group:

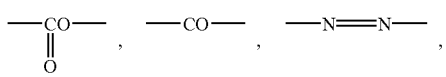

Y is a terminal polar or apolar group.

7. Composition according to claim 1, wherein each thermotropic mesogenic group is linked to the main macromolecular chain by the intermediary of a spacer.

8. Composition according to claim 7, wherein the spacer is selected from the group consisting of methylene, oxymethylene, oxyethylene and dimethylsiloxane oligomers.

9. Composition according to claim 8, wherein the oligomer has a minimal length corresponding to three monomeric motifs.

10. Composition according to claim 1, wherein the liquid crystal polymer bears maximally 50% of mesogenic groups with respect to the total mass of the polymer.

11. Composition according to claim 1, wherein the liquid crystal polymer is defined by the following structure:

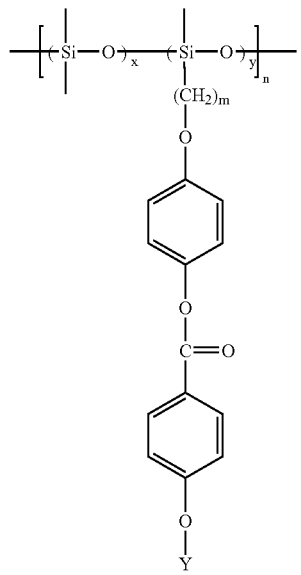

where Y is a terminal polar or apolar group, m is an integer higher than 3, n is an integer higher than 50, and x and y are such that the liquid crystal polymer bears maximally 50% of mesogenic groups with respect to the total mass of the polymer.

12. Composition according to claim 11, wherein the liquid crystal polymer results from the synthesis consisting of the following successive steps: cationic polymerization of the polydimethylsiloxane hydrogenation of the polydimethylsiloxane, then grafting of the thermotropic mesogenic groups, linked by covalent bonds to spacers, by hydroxylation to the polydimethylsiloxane.

13. Composition according to claim 1, wherein the anhydrous solvent is a silicone oil selected from the group consisting of polydimethylsiloxanes and phenylated silicones.

14. Composition according to claim 1, wherein the anhydrous solvent is a mixture containing a hydrocarbon oil which is an aromatic ester.

15. Composition according to claim 1, wherein it constitutes a care and/or treatment and/or make-up composition for the keratinic matter.

16. Composition according to claim 1, wherein the composition contains in addition at least one cosmetic active compound.

17. Composition according to claim 1, wherein the composition contains at least one additive selected from the groups consisting of water, antioxidants, essential oils, preservatives, neutralizers, liposoluble polymers, fillers, perfumes and mixtures thereof.

18. Composition according to claim 1, wherein the composition is anhydrous and available in the form of a gel at ambient temperature and in that of a fluid at the temperature of the skin of human beings.

19. Composition according to claim 1, wherein the composition is available in the form of a water-in-oil (W/O) or oil-in-water (O/W) emulsion, the consistency of which is approximately that of a gel at ambient temperature and that of a fluid at the temperature of the skin of human beings.

20. Composition according to claim 1, wherein the composition contains at least one coloring matter.

21. Composition according to claim 20, wherein the coloring matter is selected from the group consisting of lipophilic coloring matters, hydrophilic colouring matters, pigments, pearlescent preparations and mixtures thereof.

22. Composition according to claim 1, wherein the composition is available in the form of foundation make-up or a lipstick.

23. A method for caring for and/or making-up the skin and/or lips of a human being, comprising applying to the skin and/or the lips a cosmetic composition according to claim 1.

24. A process for manufacturing the cosmetic composition of claim 1 comprising dissolving at least one thermotropic liquid crystal polymer, comprising one main monomolecular chain and thermotropic mesogenic groups grafted onto the monomolecular chain, with a degree of grafting of at least 10% in at least one anhydrous solvent selected from the group consisting of hydrocarbon oils and siliconized oils, heating the solution to a temperature higher than the clarification temperature of the thermotropic liquid crystal polymer, and cooling the solution.

25. A method of making-up the skin and/or lips of a human being comprising applying the cosmetic composition of claim 1 to the skin and/or lips.

* * * * *